US00PP20639P2

(12) United States Plant Patent
Zaiger et al.

(10) Patent No.: US PP20,639 P2
(45) Date of Patent: Jan. 12, 2010

(54) PEACH TREE NAMED 'SAUZEE PRIDE'
(50) Latin Name: *Prunus persica*
Varietal Denomination: Sauzee Pride

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/316,378

(22) Filed: Dec. 12, 2008

(51) Int. Cl.
*A01H 5/00* (2006.01)

(52) U.S. Cl. ..... Plt./198

(58) Field of Classification Search ..... Plt./198
See application file for complete search history.

*Primary Examiner*—Kent L Bell

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Production of large size, peento type fruit.
3. Fruit with firm flesh, good handling and shipping qualities.
4. Yellow flesh fruit with a sweet, sub-acid flavor.
5. Fruit with very good flavor and eating quality.
6. Heavy and regular production of fruit.

1 Drawing Sheet

Botanical classification: *Prunus persica.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach and nectarine trees, which are known to us, and mentioned herein, are 'May Grand' Nectarine (U.S. Plant Pat. No. 2,794), 'Early Sun Grand' Nectarine (U.S. Plant Pat. No. 1,420), 'Royal Gold' Peach (U.S. Plant Pat. No. 2,663) and 'Saturn' Peach (U.S. Plant Pat. No. 5,123).

STATEMENT REGARDING FEDERALLY SPONSORED RESEARCH AND DEVELOPMENT

Not applicable.

ORIGIN OF THE VARIETY

A new and distinct variety of peach tree (*Prunus persica*) was originated by us in our experimental orchard located near Modesto, Calif., from seed of an open pollinated proprietary seedling with field identification number 55ZA18. The (55ZA18) seedling originated from a cross between the proprietary seedling with field identification number 207LF85 and the peento peach selection 505-13 received from the quarantine station in Beltsville. The maternal parent (207LF85) originated from crosses between 'May Grand' Nectarine (U.S. Plant Pat. No. 2,794), 'Early Sun Grand' Nectarine (U.S. Plant Pat. No. 1,420) and 'Royal Gold' Peach (U.S. Plant Pat. No. 2,663). A large group of these open pollinated seedlings were planted and maintained on their own root system, during which time we recognized the desirable peento fruit characteristic, (commonly referred to as saucer or doughnut shape) of the present new variety and.selected it for asexual propagation and commercialization in 2001.

ASEXUAL REPRODUCTION OF THE VARIETY

Asexual reproduction of the new and distinct variety of peach tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous upright growth and a productive and regular bearer of large size, yellow flesh, freestone fruit with very good eating quality. The fruit is further characterized with having a slight orange-red blush, having a mild, sweet, sub-acid flavor, being peento in shape, with firm flesh and having greater handling and shipping quality than most peento peach varieties. The tree has a winter chilling requirement of approximately 750 hours at or below 45° F. and is hardy in all stone fruit growing areas of California. In comparison to its seed peento peach parent (55ZA18) the new variety is larger in size, has yellow flesh compared to white and is 4 to 5 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color.

Tree:

*Size.*—Large, pruned to 3 to 3.5 meters in height for economical harvesting of fruit. Average spread 3 meters, varies with cultural practices.

*Vigor.*—Vigorous, growth of 1.5 meters in height the first growing season. Varies with soil type, fertility and cultural practices.

*Form.*—Upright, usually pruned to vase shape.

*Branching habit.*—Upright, crotch angle approximately 35°, increases with crop load.

*Productivity.*—Productive, thinning and spacing of fruit necessary. Number of fruit set varies with climatic conditions during blooming period.

*Bearer.*—Regular, adequate fruit set 4 consecutive years. No alternate bearing observed.

*Fertility.*—Self fertile.

*Density.*—Medium dense, usually pruned to vase shape by removing center branches and foliage which increases sunlight and air movement to center of tree.

*Hardiness.*—Hardy in all stone fruit growing areas in California. Tree grown in USDA Hardiness Zone 9. Winter chilling requirement approximately 750 hours at or below 45° F.

Trunk:

*Size.*—Medium. Average circumference 50.8 cm at 20.3 cm above ground on 7 year old tree.

*Stocky.*—Medium stocky.

*Texture.*—Medium shaggy, becomes rougher with age.

*Color.*—Varies from 10YR 3/2 to 2.5YR 4/2.

Branches:

*Size.*—Medium. Average circumference 18.4 cm at 1 meter above ground. Crotch angle approximately 35°, increases with crop load.

*Surface texture.*—New growth relatively smooth. Mature growth medium rough, roughness increases with age.

*Lenticels.*—Average number of 28 in a 25.8 sq cm section. Average length 4.4 mm. Average width 1.5 mm. Color varies from 7.5YR 5/8 to 7.5YR 4/8.

*Color.*—New growth varies from 2.5GY 6/6 to 5GY 5/8. Mature growth varies from 7.5YR 3/4 to 10YR 3/4, varies with age of growth.

Leaves:

*Size.*—Large. Average length 161.1 mm. Average width 40.5 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins. Lower surface relatively smooth, small ridges created by midrib and pinnate venation. Both surfaces glabrous.

*Petiole.*—Average length 13.5 mm. Average width 1.6 mm. Longitudinally grooved. Surface glabrous. Color varies from 2.5GY 5/6 to 5GY 5/8.

*Stipules.*—Average number at shoot tip — 2, varies from 2 to 4. Average number at base of leaf petiole — 2. Margin — pectinate. Color varies from 5GY 4/8 to 5GY 5/6.

*Glands.*—Type — reniform. Size — medium to large. Average length 1.6 mm. Average diameter 0.8 mm. Average number 4, varies from 2 to 6. Location — primarily on base of leaf blade, upper portion of petiole. Color varies from 5GY 5/6 to 5GY 5/8.

*Color.*—Upper surface varies from 5GY 4/4 to 5GY 3/6. Lower surface varies from 5GY 5/4 to 5GY 4/4. Midvein color varies from 10Y 8/6 to 2.5GY 8/6.

Flower buds:

*Size.*—Large. Average length 19.5 mm. Average width 10.0 mm.

*Hardiness.*—Hardy with respect to California winters.

*Form.*—Conical, becoming elongated before opening.

*Pedicel.*—Average length 3.9 mm. Average width 0.9 mm. Color varies from 2.5GY 5/8 to 5GY 5/6.

*Color.*—Varies from 7.5RP 6/12 to 5RP 8/6.

Flowers:

*Size.*—Large to extra large, showy. Average height 19.9 mm. Average diameter 45.5 mm.

*Petals.*—Normally 5, alternately arranged to sepals. Form — ovate, narrows at point of attachment. Average length 21.8 mm. Average width 17.2 mm. Margin — entire. Color varies from 5RP 8/4 to 5RP 8/6, fades with age of flower. Both surfaces glabrous.

*Sepals.*—Normally 5, alternately arranged to petals. Medium to large. Average length 6.5 mm. Average width 5.3 mm. Shape — triangular, apex rounded. Margin — entire. Surface — upper surface glabrous, lower surface pubescent. Color — upper surface 5GY 5/6 to 5GY 5/8. Lower surface 5R 2/6 to 2.5R 3/4.

*Stamens.*—Average number — 50. Average filament length 16.2 mm. Filament color varies from 5RP 9/2 to 5RP 8/4. Anther color varies from 5R 3/10 to 7.5R 3/12.

*Pollen.*—Self fertile. Color varies from 5Y 7/10 to 2.5Y 7/10.

*Pistil.*—Usually one. Surface — pubescent. Average length 21.0 mm. Stigma height approximately same as anthers. Color varies from 7.5Y 8.5/6 to 7.5Y 8/6.

*Fragrance.*—Moderate.

*Blooming period.*—Date of First Bloom Mar. 1, 2008. Date of Petal Fall Mar. 10, 2008, varies slightly with climatic conditions.

*Color.*—Varies from 5RP 7/6 to 5RP 7/8.

*Number flowers per flower bud.*—Usually one.

*Pedicel.*—Average length 5.2 mm. Average width 1.3 mm. Color 5GY 5/6 to 5GY 5/8.

Fruit:

*Maturity when described.*—Firm ripe.

*Date of first picking.*—Jul. 16, 2008.

*Date of last picking.*—Jul. 22, 2008, varies slightly with climatic conditions.

*Size.*—Large. Average diameter axially 47.7 mm. Average transversely in suture plane 87.5 mm. Average weight 244.2 grams, varies slightly with fertility of soil, amount of thinning and climatic conditions.
*Form.*—Peento shape.
*Suture.*—Distinct, extends from base toward apex, usually ending at highest point near apex.
*Ventral surface.*—Lipped, well sealed.
*Apex.*—Retuse.
*Base.*—Retuse.
*Cavity.*—Rounded to slightly elongated in suture plane. Average depth 3.5 mm. Average diameter 14.4 mm.

Stem:
*Size.*—Small. Average length 6.2 mm. Average diameter 4.0 mm.
*Color.*—Varies from 7.5Y 5/8 to 10Y 5/8.

Flesh:
*Ripens.*—Relatively even.
*Texture.*—Firm, meaty.
*Fibers.*—Few, small, tender.
*Firmness.*—Good flesh firmness, much firmer than the commercial peento peach 'Saturn' (U.S. Plant Pat. No. 5,123).
*Aroma.*—Moderate, good peach aroma.
*Amydgalin.*—Undetected.
*Eating quality.*—Very good.
*Flavor.*—Very good, sweet, sub-acid flesh.
*Juice.*—Moderate, enhances flavor.
*Brix.*—Average 10.2°, varies slightly with amount of fruit per tree and climatic conditions.
*Color.*—Varies between 2.5Y 8.5/12 to 5Y 8.5/6.
*Pit cavity.*—Slight bleeding around pit cavity. Color varies from 2.5Y 8/8 to 5R 4/12. Average length 18.6 mm. Average width 29.3 mm. Average depth 13.1 mm.

Skin:
*Thickness.*—Medium.
*Surface.*—Smooth.
*Pubescence.*—Moderate amount, short in length.
*Tendency to crack.*—Very slight, primarily at apex.
*Color.*—Ground color varies from 2.5Y 8/8 to 5Y 8/8. Slight blush color varies from 5R 5/8 to 7.5R 6/8.
*Tenacity.*—Tenacious to flesh.
*Astringency.*—Very slight.

Stone:
*Type.*—Freestone.
*Size.*—Medium. Average length 17.9 mm. Average width 28.1 mm. Average thickness 25.1 mm.
*Form.*—Peento shape, resembling shape of fruit.
*Base.*—Nearly flat.
*Apex.*—Nearly flat, only slightly rounded.
*Surface.*—Pitted throughout, pits vary from round to elongated.
*Sides.*—Unequal, one side extending further from suture plane.
*Ridges.*—Small, narrow, ridges running from base toward apex, sharp.
*Tendency to split.*—None.
*Color.*—Varies from 7.5YR 3/6 to 10YR 3/6 when dry.

Kernel:
*Size.*—Medium. Average length 8.1 mm Average width 13.8 mm. Average depth 12.0 mm.
*Form.*—Ovate, more round than most peach kernels.
*Taste.*—Bitter.
*Viability.*—Viable, complete embryo development.
*Skin.*—Color varies from 5Y 8.5/8 to 5Y 8/8 when dry.

Use: Dessert.
*Market.*—Local and long distance.

Keeping quality: Good, held firm for 2 weeks at 38° to 42° F. without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

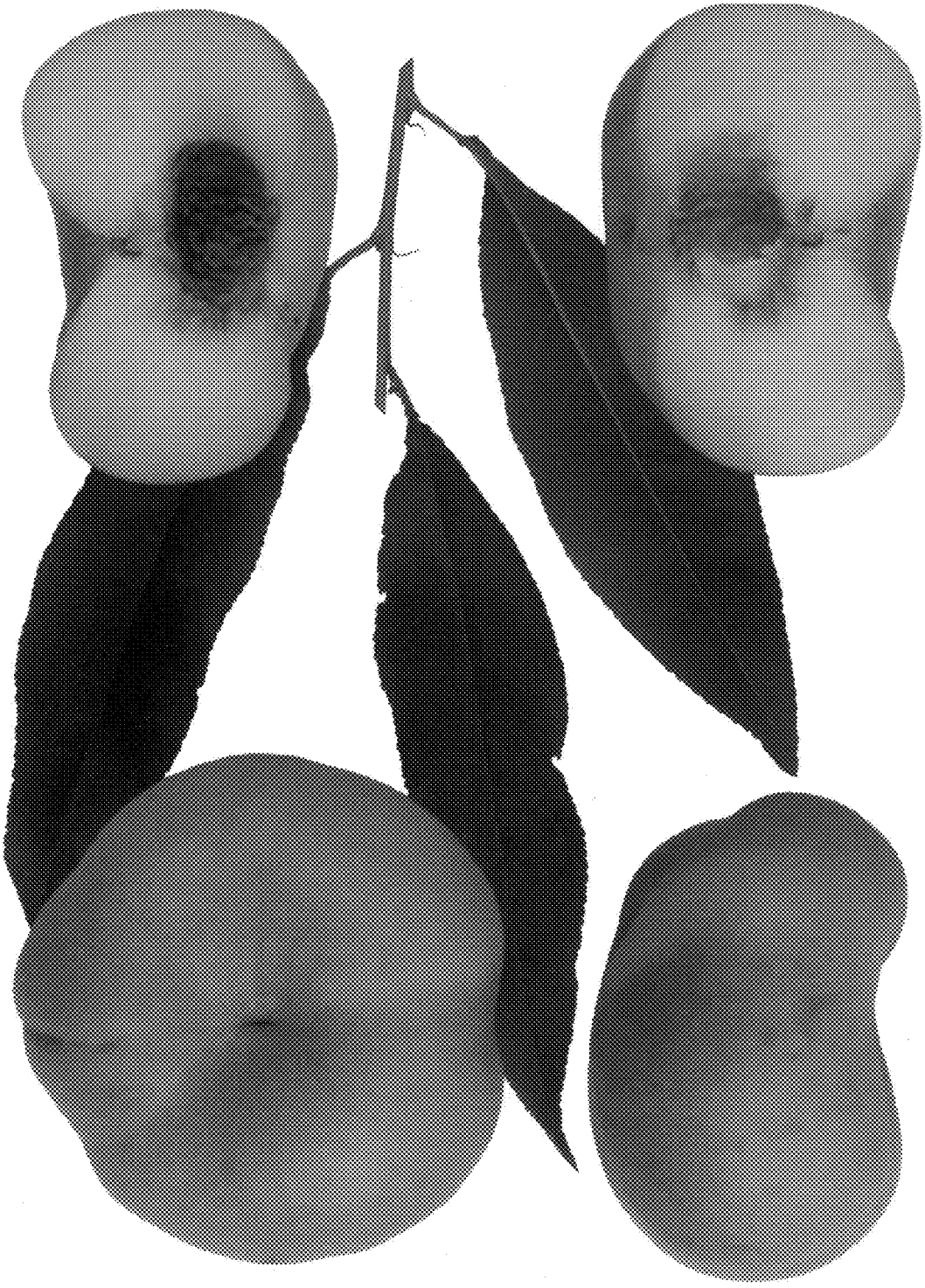

* * * * *